US006046368A

United States Patent [19]
Lamanna et al.

[11] Patent Number: 6,046,368
[45] Date of Patent: Apr. 4, 2000

[54] CATALYTIC PROCESS FOR MAKING HYDROFLUOROETHERS

[75] Inventors: William M. Lamanna, Stillwater; Richard M. Flynn, Mantomedi; Daniel R. Vitcak, Cottage Grove; Zai-Ming Qiu, Woodbury, all of Minn.

[73] Assignee: 3M Innovative Properties Company, Saint Paul, Minn.

[21] Appl. No.: 09/042,819

[22] Filed: Mar. 17, 1998

[51] Int. Cl.[7] .................................................. C07C 41/00
[52] U.S. Cl. ........................................... 568/683; 568/681
[58] Field of Search ................................ 568/681, 683, 568/419

[56] References Cited

U.S. PATENT DOCUMENTS

| | | | |
|---|---|---|---|
| 2,519,983 | 8/1950 | Simons | 204/62 |
| 4,357,282 | 11/1982 | Anderson et al. | 260/544 F |
| 5,466,877 | 11/1995 | Moore | 562/852 |
| 5,554,664 | 9/1996 | Lamanna et al. | 522/25 |
| 5,750,797 | 5/1998 | Vitcak et al. | 566/683 |

FOREIGN PATENT DOCUMENTS

| | | | |
|---|---|---|---|
| 2287432 | 7/1976 | France | C07C 43/12 |
| 1 294 949 | 5/1969 | Germany | C07C 43/12 |
| 6-293686 | 10/1994 | Japan | C07C 43/12 |
| WO 96/36689 | 11/1996 | WIPO | C11D 7/50 |

OTHER PUBLICATIONS

W. V. Childs et al., "Anodic Fluorination," *Organic Electrochemistry*, Marcel Dekker, Inc., 1991, pp. 1103–1127.
S. Nagase, "Electrochemical Fluorination," *Fluorine Chemistry Reviews*, Marcel Dekker, Inc., 1967, pp. 77–106.
D. England, "Catalytic Conversion of Fluoroalkyl Alkyl Ethers to Carbonyl Compounds," *Journal of Organic Chemistry*, vol. 49, 1984, pp. 4007–4008.
P. Zurer, "Looming Ban on Production of CFC's Halons Spurs Switch to Substitutes," *Chemical & Engineering News*, Nov. 1993, pp. 12–18.
C. G. Krespan et al., "The Chemistry of Highly Fluorinated Carbocations," *Chem. Rev.* vol. 96, 1996, pp. 3269–3301.
T. Cheung et al., "Strong Solid–Acid Catalysts for Paraffin Conversions," *Chemtech*, vol. 27, No. 9, Sep. 1997, pp. 28–35.
G. A. Olah, "Solid Superacids," John Wiley & Sons, Inc., 1985, pp. 53–64.
R. Drago, Inorg. Chem., vol. 29, 1990, pp. 1186–1192.

*Primary Examiner*—Elli Peselev
*Attorney, Agent, or Firm*—Lisa M. Fagan

[57] ABSTRACT

Briefly, in one aspect, this invention provides a catalytic method of preparation of primary and secondary hydrofluoroethers, the process comprising reacting a fluorinated precursor material and an alkylating agent in the presence of a Lewis acid catalyst or a mixture comprising Lewis acid and Bronsted acid catalysts.

26 Claims, No Drawings

CATALYTIC PROCESS FOR MAKING HYDROFLUOROETHERS

FIELD OF THE INVENTION

This invention relates to a method of producing hydrofluoroethers. More particularly, the present invention relates to the catalytic production of hydrofluoroether compounds by the alkylation of certain carbonyl-containing compounds.

BACKGROUND OF THE INVENTION

Chlorofluorocarbon compounds (CFCs) and hydrochlorofluorocarbon compounds (HCFCs) as a class possess unique chemical stability and solvent properties and have until only recently been used in a wide variety of applications, finding utility in drying processes, cleaning processes (e.g., the removal of flux residues from printed circuit boards), and vapor degreasing applications. While these materials were initially believed to be environmentally benign, they now are linked to ozone depletion. According to the Montreal Protocol and its attendant amendments, production and use of CFCs must be discontinued (see, e.g., P.S. Zurer, *Looming Ban on Production of CFCs, Halons Spurs Switch to Substitutes*, CHEM. & ENG'G NEWS, Nov. 15, 1993, at 12). Characteristics sought in CFC and HCFC replacements, in addition to low ozone depletion potential, typically include low flammability, and low toxicity, and boiling point ranges that are suitable for a variety of solvent cleaning applications. Such replacement solvents also should have the ability to dissolve both hydrocarbon-based and fluorocarbon-based soils.

A group of compounds spotlighted recently as promising substitutes for ozone-depleting solvents are hydrofluoroethers. These compounds, as a class, are particularly promising candidates not only because of their zero ozone-depleting potential, but also because they exhibit very useful solvent properties.

A number of synthetic routes to hydrofluoroethers are known. These methods may be broadly divided into two groups; methods of fluorinating an ether compound, and methods where the ether linkage is formed within a compound by reaction with a fluorine-containing precursor. The former methods include: (1) direct fluorination of an ether compound; and (2) electrochemical fluorination of an ether compound. The latter methods include: (3) the addition reaction of an alcohol to a fluorinated olefin; (4) alkylation of a partially fluorinated alcohol; and (5) non-catalytic alkylation of a fluorinated carbonyl compound with a suitable alkylating agent. Japanese Patent No. JP 6-293686 provides a partial summary description of these varied methods.

Suitable methods for alkylation of fluorinated compounds include those described by French Patent Publication No. 2,287,432 and German Patent Publication No. 1,294,949, and such useful non-catalytic alkylation processes typically comprise the reaction of a perfluorinated acyl fluoride or a perfluorinated ketone with an anhydrous source of fluoride ion (e.g., an alkali metal fluoride such as potassium fluoride, cesium fluoride, or silver fluoride) in an anhydrous polar, aprotic solvent to produce a perfluorinated alkoxide that subsequently is reacted with a suitable alkylating agent such as a dialkyl sulfate, an alkyl halide, or an alkyl perfluoroalkanesulfonate, to produce a primary or secondary hydrofluoroether.

A more recent advance with respect to the above alkylation processes is described by published patent application WO 96/36689 that provides a method of non-catalytic alkylation of fluorinated carbonyl compounds in the presence of a tertiary or aromatic amine.

While the alkylation processes described above may be commercially viable as they are practiced in the art, there is continuing need to improve the economic efficiencies of commercially employed methods of production. In the interests of optimizing the overall process, there also is an ever-present and strong interest in increasing product yields and purities and in decreasing raw material and waste disposal costs. The elimination of potentially toxic alkylating agents such as the commonly used dimethyl sulfate from these reactions also would present significant safety benefits.

SUMMARY OF THE INVENTION

Briefly, in one aspect, this invention provides an improved alkylation process for the preparation of hydrofluoroether compounds, said process comprising:

(1) reacting in the presence of at least one Lewis acid catalyst or a mixture comprising Lewis acid and Bronsted acid catalysts:

a) a fluorinated ketene or a fluorinated carbonyl-containing compound of the formula:

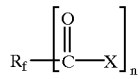

wherein n is an integer equal to 1, 2 or 3; and when n is 1, $R_f$ is a fluorine atom or is a fluorinated, preferably perfluorinated, alkyl group having from 1 to about 15 carbon atoms that may be substituted or unsubstituted, saturated or unsaturated, cyclic or acyclic linear or branched and may optionally contain one or more catenary heteroatoms such as nitrogen, sulfur, or oxygen;

when n is 2, $R_f$ is a fluorinated, preferably perfluorinated, alkylene group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen;

when n is 3, $R_f$ is a fluorinated, preferably perfluorinated, alkylidene group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen; and wherein each non-fluorine substituent on the above $R_f$ group may optionally include —Cl, —H, —Br, —SO$_2$X, or —SO$_2$R'—COX, —CO$_2$R', or —OR' where R' is a fluorinated or non-fluorinated alkyl group; and wherein each X is independently a hydrogen or a halogen atom, preferably fluorine, or is of the formula R'$_f$ or OR'$_f$ where R'$_f$ is a partially or fully fluorinated or non-fluorinated alkyl group having from 1 to about 10 carbon atoms that may be substituted or unsubstituted, saturated or unsaturated, cyclic or acyclic, linear or branched and may optionally contain one or more catenary heteroatoms such as nitrogen, sulfur, or oxygen; where X is an R'$_f$ group, that R'$_f$ group may form a ring with the $R_f$ group previously defined such as would give, e.g., a cyclic ketone; and b) an alkylating agent of the general formula:

R—F wherein:
R is a substituted or unsubstituted, saturated or unsaturated, cyclic or acyclic, linear or branched, non-halogenated or partially halogenated alkyl group having from 1 to about 10 carbon atoms that can optionally include one or more catenary heteroatoms such as oxygen, nitrogen or sulfur, where if said R group is substituted, the non-hydrogen substituents may optionally include —Cl, —Br, —F, —SO$_2$X', —SO$_2$R', —COX', —COR', —CO$_2$R', or —OR' (where R' is as defined above and where X' is a halogen atom, preferably F); and (2) recovering hydrofluoroether product from the resulting mixture.

In another embodiment, the present invention provides an alkylation process for the preparation of hydrofluoroether compounds, said process comprising:

(1) reacting in the presence of at least one Lewis acid catalyst or a mixture comprising Lewis acid and Bronsted acid catalysts:
a) a fluorinated mono- or polyether compound or a fluorinated oxacycloalkane with
b) an alkylating agent of the general formula:

R—F wherein:
R is a substituted or unsubstituted, saturated or unsaturated, cyclic or acyclic, linear or branched, non-halogenated or partially halogenated alkyl group having from 1 to about 10 carbon atoms that can optionally include one or more catenary heteroatoms such as oxygen, nitrogen or sulfur, where if said R group is substituted, the non-hydrogen substituents may optionally include —Cl, —Br, —F, —SO$_2$X', —SO$_2$R'—COX', —COR', —CO$_2$R', or —OR' (where R' is as defined above and where X' is a halogen atom, preferably F); and (2) recovering hydrofluoroether product from the resulting mixture.

In yet another embodiment, the present invention provides an alkylation process for the preparation of hydrofluoroether compounds, said process comprising:

(1) reacting in the presence of at least one Lewis acid catalyst or a mixture comprising Lewis acid and Bronsted acid catalysts:
a) a fluorinated mono- or polyether compound with
b) a fluorinated ketene or a fluorinated carbonyl-containing compound of the formula:

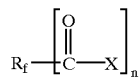

where R$_f$, X and n are as previously defined; and
2) recovering hydrofluoroether product from the resulting mixture.

DETAILED DESCRIPTION OF PREFERRED EMBODIMENTS

The catalytic processes provided herein afford myriad, important advantages over other state of the art alkylation methods useful for the production of hydrofluoroether materials. Among such advantages, the subject catalytic processes may be carried out in the absence of additional solvent, a benefit that minimizes raw material cost and improves reactor efficiency. Additionally, as compared to those methods taught by the prior art, the methods of the invention do not require the use of potassium fluoride, toxic alkylating agents such as dimethyl sulfate, phase transfer agents, or amines such as trialkyl amines. These processes also produce no waste salts and are not adversely affected by the presence of HF, a contaminant commonly found in fluorinated starting materials. These reactions proceed rapidly under mild conditions to achieve a relatively high yield of many hydrofluoroether products while generating minimal undesired side products. The described methods also can be adapted to continuous operation and, with the exception of spent catalyst, generate negligible waste by-products.

The hydrofluoroether compounds made in accordance with the invention may include those represented by the following general formula:

(I)

wherein x is 1 to 3; and when x is 1, R$_f$ is a fluorinated, preferably perfluorinated, alkyl group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen;

when x is 2, R$_f$ is a fluorinated, preferably perfluorinated, alkylene group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen;

when x is 3, R$_f$ is a fluorinated, preferably perfluorinated, alkylidene group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen; and wherein each non-fluorine substituent on the above R$_f$ group may optionally include —Cl, —H, —Br, —SO$_2$X, —SO$_2$R'—COX, —CO$_2$R', —COR', or —OR' where X a halogen atom, preferably F and where R' is a fluorinated or non-fluorinated alkyl group; and wherein each R is independently selected as a substituted or unsubstituted, saturated or unsaturated, cyclic or acyclic, linear or branched, non-halogenated, or partially halogenated alkyl group having from 1 to about 10 carbon atoms where if R is substituted, the non-hydrogen substituents may include —Cl, —F, —Br, —SO$_2$R', —SO$_2$X, —COX, —COR', —CO$_2$R', or —OR' where R' and X are as defined above, and where R may optionally otherwise also contain one or more catenary heteroatoms such as oxygen, sulfur or nitrogen.

Examples of compounds suitable for alkylation according to the invention include fluorinated acyl halides, preferably fluorinated acyl fluorides, fluorinated aldehydes, fluorinated ketones and fluorinated ketenes; preferably such compounds are perfluorinated. Useful fluorinated ketenes include those of the formula:

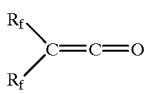
(II)

where each $R_f$ is selected, independently from one another, as a fluorine atom or as a fluorinated, preferably perfluorinated, alkyl group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen.

Other useful classes of carbonyl-containing compounds may be represented generally by the following formula:

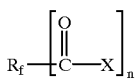
(III)

wherein n is an integer equal to 1, 2 or 3; and when n is 1, $R_f$ is a fluorine atom or is a fluorinated, preferably perfluorinated, alkyl group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen;

when n is 2, $R_f$ is a fluorinated, preferably perfluorinated, alkylene group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen;

when n is 3, $R_f$ is a fluorinated, preferably perfluorinated, alkylidene group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen; and wherein each non-fluorine substituent on the above $R_f$ group may optionally include —Cl, —H, —Br, —SO$_2$X, —SO$_2$R'—COX, —CO$_2$R', or —OR' where R' is a fluorinated or non-fluorinated alkyl group; and each X is independently a hydrogen or a halogen atom, preferably fluorine, or is of the formula $R'_f$ or $OR'_f$ where $R'_f$ is a partially or fully fluorinated or non-fluorinated alkyl group having from 1 to about 10 carbon atoms that may be substituted or unsubstituted, saturated or unsaturated, cyclic or acyclic, linear or branched and may optionally contain one or more catenary heteroatoms such as nitrogen, sulfur, or oxygen; where X is an $R'_f$ group, that $R'_f$ group may form a ring with the $R_f$ group previously defined such as would give, e.g., a cyclic ketone.

Among the classes of carbonyl-group containing compounds depicted above by Formulas II and III useful as starting materials for the process invention are the following, representative examples:

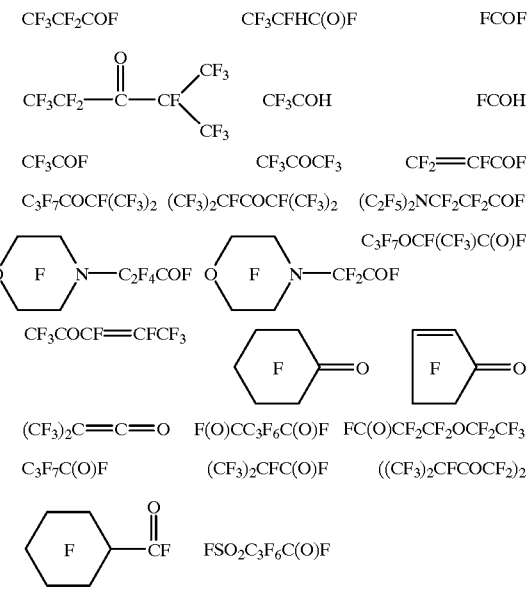

Useful perfluorinated acyl halides can be prepared, for example, by electrochemical fluorination (ECF) of a corresponding hydrocarbon carboxylic acid, or derivative thereof such as a carboxylic acid halide, anhydride or ester, using either anhydrous hydrogen fluoride ("Simons" ECF) or KF.2HF ("Phillips" ECF) as an electrolyte. Details of the "Simons" ECF process may be found in U.S. Pat. No. 2,519,983 (Simons) and by S. Nagase in 1 FLUORINE CHEM. REV. 77, 77–106 (1967). W. V. Childs et al, *Anodic Fluorination, in* ORGANIC FLUOROCHEMISTRY 1103–04, 1113–17 (Henning Lund & Manuel M. Baizer eds., 1991) provide a description of the "Phillips" ECF process.

Perfluorinated acyl halides and perfluorinated ketones also can be prepared by disproportionation of perfluorinated carboxylic acid esters (that can be prepared from the corresponding hydrocarbon or partially-fluorinated carboxylic acid esters by direct fluorination with fluorine gas). Disproportionation can be achieved by contacting the perfluorinated ester with a source of fluoride ion (see the method described in U.S. Pat. No. 5,466,877 (Moore), whose description is incorporated herein by reference) or by combining the ester with at least one initiating reagent selected from the group consisting of: gaseous, non-hydroxylic nucleophiles; liquid, non-hydroxylic nucleophiles; and mixtures of at least one non-hydroxylic nucleophile (gaseous, liquid, or solid) and at least one solvent that is inert to acylating agents. Alternatively, disproportionation can be achieved by contacting certain perfluorinated esters with a catalytic amount of an acid catalyst. This acid-catalyzed disproportionation may be effected in a prior step to produce perfluorinated acyl fluorides or may be used to generate perfluorinated acyl fluorides in-situ. Acid catalysts that are effective in catalyzing the disproportionation of the perfluorinated esters include those claimed in the present invention.

In one embodiment of the invention, carbonyl-containing compounds are generated in situ under the conditions of the catalytic alkylation process and the in situ generated carbonyl compound may, in turn, be catalytically alkylated to form the hydrofluoroether product. Thus certain fluorinated compounds may be employed in the catalytic alkylation reaction that do not have a carbonyl group per se, but have a moiety that is readily converted to a carbonyl group under the conditions of this process, such as upon exposure to a Lewis acid catalyst or a mixture of Lewis acid/Bronsted acid catalysts. These latter compounds include, generally, fluorinated mono- or polyether compounds and fluorinated oxacycloalkanes. Many useful mono- and polyethers include those described in U.S. Pat. No. 4,357,282, whose description is incorporated by reference herein. Useful oxacycloalkanes can be substituted or unsubstituted, saturated and unsaturated, and can be partially or fully fluorinated and include, for example, oxacyclopropanes, oxacyclobutanes and oxacyclopentanes. Oxacycloalkanes containing strained ring systems are most susceptible to acid-catalyzed rearrangement to the ring opened carbonyl compound; thus oxacyclopropanes and oxacyclobutanes are preferred.

Useful mono- and polyethers include those depicted by the formula:

$$R^1O(R^2O)_yR^3 \qquad (IV)$$

wherein y is 0 or is an integer greater than or equal to 1 and $R^1$, $R^2$, and $R^3$ each is independently selected as a non-fluorinated or a partially or fully fluorinated, substituted or unsubstituted, linear or branched, cyclic or acyclic, saturated or unsaturated alkyl group having from 1 to about 10 carbon atoms with the proviso that at least one of said $R^1$, $R^2$, or $R^3$ groups is fluorinated.

It must be understood with respect to the above fluorinated mono- and polyether compounds, that while this class as described include compounds that are potential products of the alkylation reactions of the invention, it may be desirable to utilize the methods of this invention to convert one fluorinated ether into another, and such conversions expressly are included within the scope hereof.

Representative of the above classes of compounds that do not contain a carbonyl-group include, but are not limited to, the following:

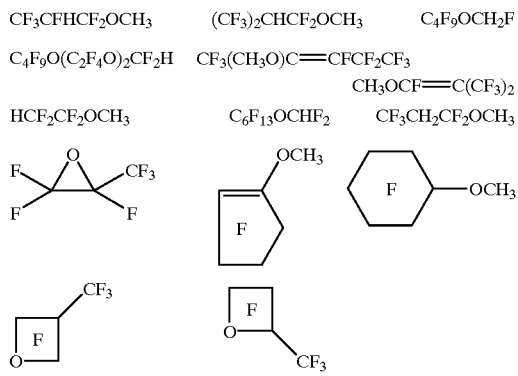

These compounds shown above may be used to generate useful carbonyl compounds in a prior step or in situ, as shown in the table below depicting the in situ conversion for representative starting ether compounds.

| Starting Ether | Generated Carbonyl Compound | Byproduct |
|---|---|---|
| $CF_3CFHCF_2OCH_3$ | $CF_3CFHCOF$ | $CH_3F$ |
| $(CF_3)_2CHCF_2OCH_3$ | $(CF_3)_2CHCOF$ | $CH_3F$ |
| $C_4F_9OCH_2F$ | $C_3F_7COF$ | $CH_2F_2$ |
| $HCF_2CF_2OCH_3$ | $HCF_2COF$ | $CH_3F$ |
| $C_6F_{13}OCF_2H$ | $C_5F_{11}COF$ | $CF_3H$ |

| Starting Ether | Generated Carbonyl Compound | Byproduct |
|---|---|---|
| (oxacyclopropane with F, CF_3) | $CF_3(CO)C_2F5 + C_3F_7COF$ | — |
| (oxacyclopropane with F, CF_3) | $CF_3(CO)CF_3$ | — |
| $CF_3C(OCH_3)=CFCF_2CF_3$ | $CF_3(CO)CF=CFCF_3$ | $CH_3F$ |
| $CF_3CH_2CF_2OCH_3$ | $CF_3CH_2COF$ | $CH_3F$ |
| $(C_4F_9OC_2F_4O)_2CF_2$ | $C_4F_9OCF_2COF$ | |
| $CH_3OCF=C(CF_3)_2$ | $O=C=C(CF_3)_2 +$ $F(CO)C(CF_3)=CF_2$ | $CH_3F$ |
| (cyclopentene with OCH_3, F) | (cyclopentenone with F) | $CH_3F$ |

Fluorinated mono- and polyether compounds useful as precursors to carbonyl-containing compounds may be prepared by a variety of methods known in the art as previously described. Fluorinated oxacyclopropanes may be prepared, for example, by the oxidation of the corresponding fluorinated olefins using molecular oxygen, hypochlorite or other oxygen transfer agents. Fluorinated oxacyclobutanes and oxacyclopentanes may be prepared by the fluorination of the corresponding hydrocarbon oxacycloalkanes using a variety of fluorination techniques including direct fluorination, electrochemical fluorination or by the Phillip fluorination process. The latter materials also may be separated as by-products in the production of perfluoroacyl fluorides by electrochemical fluorination.

In another embodiment of the invention, carbonyl-containing compounds may be transformed in situ to isomeric or different carbonyl compounds under the conditions of the catalytic alkylation process, and the latter carbonyl compounds may, in turn, be catalytically alkylated. For example, a fluorinated ketene may undergo rearrangement to a fluorinated acid fluoride (or the reverse) which may then undergo catalytic alkylation to form a hydrofluoroether.

Alkylating agents useful for reaction with the carbonyl-group containing compounds or carbonyl precursors described above encompass any of a large number of known alkyl fluoride alkylating agents. It will be understood that the selection of a given alkylating agent will depend in large measure on the desired hydrofluoroether product; the alkyl group in the alkylating agent will determine one side of the ether linkage. Thus, for example, if 1-methoxy nonafluoroisobutane is a desired ether product, an alkylating agent having a methyl substituent (such as methyl fluoride) must be used. To ensure an adequate yield of desired product, the alkylating agent must be reacted with the fluorinated carbonyl-containing compound at least stoichiometrically, i.e., in a 1:1 molar ratio. Preferably, however, to favor maximum yield, an excess of alkylating agent is used. Typically, the molar ratio of alkylating agent to carbonyl compound ranges from about 1:1 to about 5:1, and preferably ranges from about 1.5:1 to about 2:1.

Useful alkylating agents include any of a large number of substituted and unsubstituted alkyl fluorides with one or more reactive C—F bonds. Any such substituents on the alkyl group may include —Cl, —Br, —F, —COX', —CO₂R', —SO₂X', SO₂R', COR' or —OR' (where X', R' and R are as hereinbefore defined), provided, however, that the alkylating agent does not readily undergo competing side reactions under the catalytic alkylation conditions and that the alkylating agent does not deactivate the catalyst.

The most useful alkylating agents will be those described by the general formula:

R—F  (V)

wherein:
R is a substituted or unsubstituted, saturated or unsaturated, cyclic or acyclic, linear or branched, non-halogenated or partially halogenated alkyl group having from 1 to about 10 carbon atoms that can optionally include one or more catenary heteroatoms such as oxygen, nitrogen or sulfur, where if said R group is substituted, the non-hydrogen substituents may optionally include —Cl, —Br, —F, —SO₂X', —SO₂R', —COR', —COX', —CO₂R', or —OR' (where R' is as defined above and where X' is a halogen atom, preferably fluorine).

Representative alkylating agents include the following: CH₂F₂, CF₃H, CF₃CFH₂, CF₃CH₃, C₂H₅F, CH₃F, and CFClH₂. Preferred alkylating agents include CH₂F₂, CH₃F, and C₂H₅F.

It will also be understood that certain of the alkylating agents described above by Formula V also may be generated in situ, for example: by the reaction of ethylene with hydrogen fluoride to produce ethyl fluoride; by the catalytic transhalogenation of an alkyl halide with a source of fluoride ion (e.g., HF); or by the acid-catalyzed dealkylation of a hydrofluoroether as described in U.S. Pat. No. 4,357,282 and incorporated herein by reference, such as is illustrated by:

(CF₃)₂CHCF₂OCH₃→(CF₃)₂CHC(O)F+CH₃F  (VI)

The alkylation process of the invention is accomplished by contacting the fluorinated carbonyl compound and the alkylating agent with a small amount (normally not exceeding about 20 mol % of the limiting reactant) of catalyst or mixture of catalysts comprising one or more strong Lewis acids or a mixture of strong Lewis and strong Bronsted acids. Many of the catalysts and catalyst mixtures useful for this purpose are described by U.S. Pat. No. 4,357,282 (Anderson et al.) whose description is incorporated herein by reference. These acid catalysts may be liquids, solids or gases and may be supported on an inert substrate such as silica, graphite or alumina or on a polymeric support such as a fluorinated sulfonic acid resin (e.g., Nafion™ resin available from DuPont); a technique particularly advantageous for continuous processing. In a preferred embodiment liquid or gaseous reactants would react upon contact with a heterogeneous or supported catalyst in a stirred or fixed bed reactor.

Among the many useful acid catalysts are the following: SbF₅, HSbF₆, TiF₄, AlCl$_x$F$_{(3-x)}$(x=0-3), HF—BF₃, TaF₅, NbF₅, AsF₅, BiF₅, ZrF₄, FeF₃, SbCl₅, SbCl₂F₃, SbCl$_x$F$_{(5-x)}$, HOSO₂F/SbF₅. Combinations and mixtures of these catalysts with each other or with HF or FSO₃H also are considered useful.

Principally favored among these classes of catalysts is antimony pentafluoride, SbF₅, and catalyst mixtures containing SbF₅. Mixtures of HOSO₂F and SbF₅, including those sold under the commercial name "Magic Acid" and mixtures of SbF₅ and HF are particularly preferred. As is known, SbF₅ and HF combine to form hexafluoroantimonic acid, HSbF₆, which is substantially less viscous than the normally highly viscous and polymeric antimony pentafluoride. Antimony pentafluoride may also be combined with other Bronsted acids, including CF₃SO₃H, H—N(SO₂CF₃)₂, and H—C(SO₂CF₃)₃. Antimony pentafluoride, as well as those mixtures containing it, also may be supported on a suitable inert solid substrate. Such substrates include, but are not limited to, graphite, silica (fluorinated and not), titanium oxide (fluorinated and not), aluminum oxide (fluorinated and not), sulfonic acid resin, and any of a number of inorganic salts. Although catalysts may be used in the form of full- or partial fluorides, it is preferable for economic reasons to use as the starting catalyst non-fluorinated materials such as chlorides. These may be converted to the corresponding fluorides or mixed halo-fluorides under the reaction conditions.

The desired reaction of the above reagents may be depicted generally by the equation:

Fluorinated Carbonyl Compound + Alkylating Agent $\underset{}{\overset{[acid\ catalyst]}{\rightleftharpoons}}$ Hydrofluoroether The reaction is a reversible equilibrium, the position of which is determined by the thermodynamic parameters (ΔG°, ΔH°, ΔS°) for the reaction and the reaction conditions. High conversions to hydrofluoroether products are favored by large negative values of ΔG°. Where the alkylation reaction is exothermic (negative ΔH°), conversions generally increase as the reaction temperature is lowered.

More specifically, in reference to Formula III above, where X is F and where n is 1, the reaction may be depicted as:

R$_f$—CO—F + R—F $\overset{[SbF_5]}{\rightleftharpoons}$ R$_f$CF₂—OR and where X is R'$_f$ and n is 1:

R$_f$—CO—R'$_f$ + R—F $\overset{[SbF_5]}{\rightleftharpoons}$ R$_f$R'$_f$CF—OR which for a typical specific reaction scenario of an acid fluoride can be represented as:

C₃F₇COF + CH₃F $\overset{[SbF_5]}{\rightleftharpoons}$ C₄F₉OCH₃ and for a typical reaction scenario for a ketone can be represented as:

C₃F₇COCF₃ + CH₃F $\overset{[SbF_5]}{\rightleftharpoons}$ C₃F₇(CF₃)CFOCH₃

The reaction of the perfluorobutyrylfluoride with CH₃F in the presence of antimony pentafluoride as described immediately above proceeds rapidly under mild conditions in the absence of solvent to produce the hydrofluoroether, which remains in equilibrium with the two starting materials. Because the reaction is a reversible equilibrium, the amount of hydrofluoroether product produced is highly dependent on reaction conditions, and is particularly dependent upon temperature as well as upon the CH₃F concentration and pressure. This reaction, found to be exothermic (i.e., having a negative standard enthalpy of reaction) in the forward direction, may be manipulated to maximize hydrofluoroether yield by cooling the reaction mixture or by increasing the $CH_3F$ concentration or pressure. Also in reference to the above reaction, the position of its equilibrium is isomer dependent; higher yields of hydrofluoroether may be obtained, for example, from the normal isomer of perfluorobutyrylfluoride than with its iso isomer under identical reaction conditions.

In another embodiment of the invention, the reacting carbonyl moiety and the alkylating agent may be covalently linked and the catalytic alkylation reaction may occur in an intramolecular fashion to form a cyclic hydrofluoroether as shown below for a specific reaction scenario:

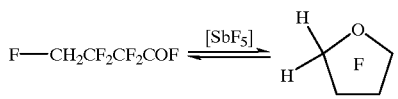

More generally, the alkylation methods of the invention may be performed in any suitable reaction vessel that is compatible with the starting materials, products and catalysts employed, although when volatile reagents are used, or when volatile products are produced, a pressure vessel is preferred. The process may be carried out by adding the fluorinated carbonyl-containing compound (or precursor), the alkylating agent (or precursor), the acid catalyst, and if employed any solvent to the reactor with moderate agitation at a temperature between approximately −120° C. and 150° C., preferably between about −70° C. and about 20° C. These reagents may be added to the reactor in any order. To minimize the possible occurrence of undesired side reactions, however, the alkylating agent is preferably the last material to be combined with the others.

The reaction equilibrium generally may be shifted to favor the hydrofluoroether product by increasing the concentration (or pressure) of the alkylating agent and/or by decreasing the reaction temperature. Where the alkylating agent is a gas, the reaction should be carried out in a sealed pressure vessel to prevent escape of the alkylating agent which if allowed to occur would shift the equilibrium in the reverse direction and thereby compromise product yield. Upon addition of all reagents to the reaction vessel, the mixture may be reacted at a temperature between about −120° C. and about 150° C., preferably between −70° C. and 20° C., and held at the reaction temperature until conversion to desired products is essentially complete or until the desired equilibrium has been reached.

Once a desired equilibrium distribution is established, the reaction may be quenched with a catalyst poison which essentially will terminate the equilibrium reaction by deactivating the catalyst and allow isolation of the desired product(s). Useful catalyst poisons for $SbF_5$ and $HF/SbF_5$ include numerous bases such as alcohols (e.g., methanol or ethanol), and water, olefins, carboxylic acids and sulfides whose selection is well known in the art. Where a heterogeneous, supported, or biphasic (i.e., two non-miscible liquid phases) catalyst is employed, it may be possible to terminate the equilibrium simply by isolating the reaction components from contact with the catalyst. This latter method may prove valuable in continuous processing schemes where fluorinated carbonyl compound and alkylating agent are fed continuously to a suitable reactor system containing a heterogeneous, supported, or biphasic catalyst and where product hydrofluoroether is collected and separated from the effluent product stream. In such a scheme, quenching of the catalyst becomes unnecessary, and any unreacted carbonyl compound and/or alkylating agent may be recycled back to the reactor.

Hydrofluoroether product may be recovered from the product mixture of either a batch or continuous reaction process using any suitable separation process. Where acid fluorides are employed and the catalytic reaction is quenched with water or alcohol, any unreacted acid fluoride is converted to its corresponding carboxylic acid or ester, respectively. These may readily be separated from the hydrofluoroether product using conventional distillation or extraction techniques. It will be understood that in carrying out the alkylation process as described herein, mixtures of hydrofluoroethers according to the general Formula I may be produced, including multiple isomers of a particular hydrofluoroether.

Since Lewis acids are employed as catalysts, it is important that all starting materials be of high purity and that the reactors be clean and dry to avoid catalyst deactivation that may be caused by certain adventitious impurities (especially basic impurities). Where acid fluorides are used as starting materials, the acid fluoride may be purified of catalyst poisons, for example, by extacting the acid fluoride with excess sulfuric acid for a period of three to five hours at room temperature followed by one-plate distillation of the acid fluoride from the $H_2SO_4$ phase. To maximize reactor volume efficiency and to minimize costs, it also is preferred to conduct the catalytic reaction in the absence of solvent. But if desired, solvents may be used, provided they are weakly coordinating, non-basic solvents that will not deactivate the catalyst. For this reason, perfluorinated solvents (e.g., alkanes, amines, and ethers), $SO_2$, $CF_3SO_3H$, anhydrous HF, $FSO_3H$, $SO_2ClF$, and $SO_2F_2$ are preferred.

The following examples are offered to aid in a better understanding of the present invention. This list is not to be construed as an exhaustive compilation of embodiments of the processes taught by this invention and the examples are not to be unnecessarily construed as limiting the scope thereof.

EXAMPLES

In the following examples, all acid fluorides were purified by fractional distillation prior to their use as reactants in the catalytic alkylation process. All other reactants and reagents were used as purchased, without further purification unless otherwise specified. GC analyses were performed on a HP-5890 gas chromatograph equipped with a ⅛" OD stainless steel column packed with Supelco™ Carbopack C connected to a thermal conductivity detector or a 30 m×0.32 mm ID glass capillary DB-5 column from J&W Scientific connected to a flame ionization detector. GC-MS analyses were performed using an HP-5890 gas chromatograph equipped with a 105 m×0.32 mm ID glass capillary RTX-200 column from Restek and interfaced with a Finnigan SSQ-70 mass spectrometer operating in chemical ionization or electron impact ionization modes. $^1H$ and $^{19}F$ NMR spectra were acquired using a Varian™ UNITY plus 400 FT-NMR spectrometer operating at 400 MHz and 376 MHz, respectively. NMR samples were spiked with a small amount of 1,4-bis(trifluoromethyl)benzene for use as a cross-integration standard in quantifying sample composition. Tetramethylsilane and $CFCl_3$ also were added as chemical shift zero references.

Example 1

Reaction of perfluorobutyrylfluoride ($C_3F_7COF$) with methyl fluoride ($CH_3F$) to produce perfluorobutylmethylether ($C_4F_9OCH_3$) using $SbF_5$ as a catalyst

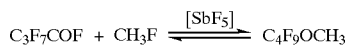

A 600 mL Parr™ Bench Top Mini Reactor (Series #4560) constructed of monel and equipped with a mechanical stirrer, thermocouple probe, dip tube, and pressure gauge was dried in an oven at 100° C., transferred to a nitrogen filled drybox and loaded with 1.88 g of $SbF_5$ catalyst (Aldrich). The reactor was reassembled and sealed under nitrogen in the drybox and then transferred to a ventilation hood where it was chilled in a dry ice bath and evacuated to 10 mTorr. The evacuated reactor was charged with 136.6 g of gaseous $C_3F_7COF$ (Purity=80.4%, 69:31 iso:normal isomer ratio; major impurities include 15.5% cyclo-$CF_2CF_2CF_2CF_2O$, 1.3% possible cyclo-$CF_2CF_2CFClCF_2O$ and 1.3% probable $CF_3CF_2CF_2OCF_3$) while maintaining dry ice cooling. The reactor then was charged in similar fashion with 29.8 g of gaseous $CH_3F$ (Purity=98+%, available from PCR).

Once all the reagents were charged, the dry ice bath was removed and the reactor was allowed to warm gradually to 30° C. over a 1.5 hour period with stirring. Heating was provided by a heating mantle and electronic temperature controller. After this brief period of warming, the dry ice bath was replaced and the reaction mixture was rapidly cooled to −25° C. and held at this temperature for approximately 30 minutes with continued stirring. A ~5 mL sample (aliquot #1) then was collected from the reactor by opening the valve on the dip tube and allowing the positive pressure within the reactor to force out the cold, liquid reaction mixture. The sample was collected under nitrogen in a dry-ice chilled Schlenck™ tube containing approximately 30 mL of methanol to immediately quench the antimony catalyst and convert any unreacted acid fluoride to the corresponding methyl ester, $C_3F_7CO_2CH_3$. The remaining reaction mixture in the reactor was allowed to cool further to −30° C. over a period of less than one hour and was then quenched by charging 230 g of anhydrous methanol (at room temperature and under nitrogen pressure) to the reactor with stirring (aliquot #2). The methanol solutions comprising aliquots 1 and 2 were allowed to warm to approximately 0° C. and then combined with approximately equal volumes of water causing the nongaseous fluorochemical components to phase split as a lower liquid phase which was separated, weighed and analyzed by gas chromatography. The total amount of fluorochemicals recovered from aliquots 1 and 2, the composition of each aliquot as determined by GC and GC-MS analysis, and the calculated percent conversion of acid fluoride to methyl ether from the GC results (overall and independently for each isomer) is summarized in Table 1.

TABLE 1

| Aliquot # | Reaction Temperature (° C.) | Recovered Fluorochemical Yield | Fluorochemical Composition (by GC Area %) | Percent Conversion [ether]/([ether] + [ester]) × 100 | |
|---|---|---|---|---|---|
| 1 | −25 | 7.4 g | 38% i-$C_4F_9OCH_3$ | Overall = | 69% |
|   |   |   | 31% n-$C_4F_9OCH_3$ | Iso = | 55% |
|   |   |   | 31% i-$C_3F_7CO_2CH_3$ | Normal = | 100% |
|   |   |   | 0% n-$C_3F_7CO_2CH_3$ |   |   |
| 2 | −30 | 83.1 g | 52% i-$C_4F_9OCH_3$ | Overall = | 83% |
|   |   |   | 31% n-$C_4F_9OCH_3$ | Iso = | 75% |
|   |   |   | 17% i-$C_3F_7CO_2CH_3$ | Normal = | 100% |
|   |   |   | 0% n-$C_3F_7CO_2CH_3$ |   |   |

Only trace amounts (<<1%) of other fluorochemical products were detected by GC or GC-MS analysis, indicating that the catalytic alkylation reaction is clean and produces few nongaseous side products. The relatively higher conversions seen for the normal isomer compared to the iso isomer suggests that branching in the $R_f$ group has a detrimental impact on the alkylation kinetics and/or equilibrium constant. The isomer ratio in the recovered product is identical to the starting acid fluoride, indicating that preferential decomposition of one of the isomers does not occur under these reaction conditions.

Example 2

Reaction of perfluorobutyrylfluoride ($C_3F_7COF$) with methyl fluoride ($CH_3F$) to produce perfluorobutylmethylether ($C_4F_9OCH_3$) using $SbF_5$ and $HSbF_6$ as a catalyst.

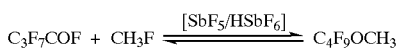

Using essentially the procedure of Example 1, the reactor was initially charged with 1.03 g of $SbF_5$ catalyst (Aldrich). The reactor was reassembled and sealed under nitrogen in the drybox and then transferred to a ventilation hood where it was chilled in a dry ice bath and evacuated to 10 mTorr. The evacuated reactor was charged with 68.3 g of gaseous $C_3F_7COF$ (Purity=80.7%, 65:35 iso:normal isomer ratio; major impurities include 12.2% cyclo-$CF_2CF_2CF_2CF_2O$, 1.5% cyclo-$CF_2CF_2CF(CF_3)O$ and 1.1% cyclo-$CF_2CF(CF_3)CF_2O$) while maintaining dry ice cooling. The reactor was then charged in similar fashion with 22.1 g of gaseous $CH_3F$ (Purity=98+%, PCR).

Once all the reagents were charged, the dry ice bath was removed and the reactor was allowed to warm gradually to 32° C. over a one hour period with stirring and then rapidly cooled back to −22° C. Gas chromatographic analysis of reaction aliquots sampled at 10° C. and at −22° C. and quenched in methanol as described in Example 1 indicated that significant alkylation of the acid fluoride to produce iso- and n-$C_4F_9OCH_3$ had occurred. However the percent conversion measured at −22° C. was not appreciably different from the conversion at 10° C., suggesting that catalyst poisoning had occurred. In order to restore catalytic activity, an additional charge of catalyst comprising 1.0 mL of $HSbF_6$ (Aldrich, triple-distilled) was added to the reactor at −80° C.

via syringe. Once catalytic activity was reestablished, the reaction mixture was allowed to equilibrate at various temperatures for at least 5 minutes after which aliquots were removed and quenched in methanol to permit determination by GC analysis of the equilibrium (or near equilibrium) distribution of products and reactants. The procedure employed to collect, quench, work up and analyze each reaction aliquot was similar to that described in Example 1. The results of this study, including the composition of the isolated fluorochemical phase and the calculated percent conversion at each temperature are summarized in Table 2 below.

Using essentially the procedure of Example 1, the reactor was initially charged with 2.04 g of $HSbF_6$ catalyst (triple-distilled, Aldrich), then with 100.8 g of gaseous $C_3F_7COF$ (Purity=80.4%, 69:31 iso:normal isomer ratio; major impurities include 15.5% cyclo-$CF_2CF_2CF_2CF_2O$, 1.3% possible cyclo-$CF_2CF_2CFClCF_2O$ and 1.3% probable $CF_3CF_2CF_2OCF_3$) while maintaining dry ice cooling. The reactor was then charged in similar fashion with 39.4 g of gaseous $CH_2F_2$ (Purity>98%, PCR).

Once all the reagents were charged, the mixture was stirred rapidly and the reaction temperature was varied between 24° C. and −76° C. while collecting reaction

TABLE 2

| Overall Reaction Time (min) | Reaction Temp. (° C.) | Aliquot # (or comment) | Fluorochemical Composition (by GC Area %) | Percent Conversion [ether]/([ether] + [ester]) × 100 | |
|---|---|---|---|---|---|
| 321 | 10 | 3 | 6.8% i-$C_4F_9OCH_3$<br>30.3% n-$C_4F_9OCH_3$<br>57.6% i-$C_3F_7CO_2CH_3$<br>5.2% n-$C_3F_7CO_2CH_3$ | Overall =<br>Iso =<br>Normal = | 37.1%<br>10.6%<br>85.4% |
| 395 | 30 | 4 | 1.6% i-$C_4F_9OCH_3$<br>23.3% n-$C_4F_9OCH_3$<br>62.1% i-$C_3F_7CO_2CH_3$<br>13.0% n-$C_3F_7CO_2CH_3$ | Overall =<br>Iso =<br>Normal = | 24.9%<br>2.5%<br>64.2% |
| 1430 | −4 | 5 | 16.4% i-$C_4F_9OCH_3$<br>28.7% n-$C_4F_9OCH_3$<br>52.6% i-$C_3F_7CO_2CH_3$<br>2.4% n-$C_3F_7CO_2CH_3$ | Overall =<br>Iso =<br>Normal = | 45.1%<br>23.8%<br>92.3% |
| 1739 | −19 | 6 | 35.2% i-$C_4F_9OCH_3$<br>29.4% n-$C_4F_9OCH_3$<br>34.8% i-$C_3F_7CO_2CH_3$<br>0.7% n-$C_3F_7CO_2CH_3$ | Overall =<br>Iso =<br>Normal = | 64.6%<br>50.3%<br>97.7% |
| 1786 | −22 | Charged reactor with 4 psi (~200 torr) anhydrous $HCl_{(g)}$ | — | — | |
| 1862 | −36 | 7 | 41.2% i-$C_4F_9OCH_3$<br>30.4% n-$C_4F_9OCH_3$<br>28.4% i-$C_3F_7CO_2CH_3$<br>0% n-$C_3F_7CO_2CH_3$ | Overall =<br>Iso =<br>Normal = | 71.6%<br>71.6%<br>100% |
| 5961 | 22 | 8 | 13.8% i-$C_4F_9OCH_3$<br>13.2% n-$C_4F_9OCH_3$<br>71.0% i-$C_3F_7CO_2CH_3$<br>2.1% n-$C_3F_7CO_2CH_3$ | Overall =<br>Iso =<br>Normal = | 27%<br>16.3%<br>86% |

The dependence of the reaction composition on temperature, as reflected in the measured distribution of quenching products and calculated conversions, indicates that the catalytic alkylation reaction is a reversible equilibrium. The shift in the reaction equilibrium in favor of the fluorinated ether products as the temperature is lowered clearly demonstrates that the alkylation reaction is exothermic; that is, the enthalpy of reaction, $\Delta H°$, is negative (in the forward direction, as written). The persistence of catalytic activity following the addition of a small amount of anhydrous HCl suggests that the catalyst is not readily deactivated by trace chloride levels.

Example 3

Reaction of iso- and n-$C_3F_7COF$ with difluoromethane ($CH_2F_2$) to form $C_4F_9OCH_2F$ using $HSbF_6$

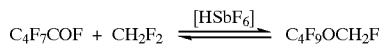

aliquots within this range to determine the effect of temperature on the distribution of reactants and products. Aliquots were removed through the dip tube and quenched under a nitrogen atmosphere in 100% ethanol at dry ice temperature to destroy the catalyst and convert unreacted acid fluoride to the corresponding ethyl ester, as described in Example 1. The alcohol solutions were allowed to warm to approximately 0° C. and then combined with approximately equal volumes of water causing the nongaseous fluorochemical components to phase split as a lower liquid phase which was separated, weighed and analyzed. The composition of each aliquot was determined by GC analysis, and GC peak assignments were verified by GC-MS and NMR analysis of selected samples. This data along with the calculated percent conversions of acid fluoride to fluoromethyl ether (overall and independently for each isomer) is summarized in Table 3.

TABLE 3

| Overall Reaction Time (min) | Reaction Temp. (° C.) | Aliquot # | Fluorochemical Composition (by GC Area %) | Percent Conversion [ether]/([ether] + [ester]) × 100 | |
|---|---|---|---|---|---|
| 325 | −55 | 4 | 1.1% n-C$_4$F$_9$OCH$_2$F | Overall = | 1.3% |
| | | | 0.2% sec-C$_4$F$_9$OCH$_2$F | Iso = | 0% |
| | | | 0% i-C$_4$F$_9$OCH$_2$F | Normal = | 3.1% |
| | | | 34.7% n-C$_3$F$_7$CO$_2$CH$_2$CH$_3$ | | |
| | | | 63.9% i-C$_3$F$_7$CO$_2$CH$_2$CH$_3$ | | |
| 1328 | −30 | 5 | 0.3% n-C$_4$F$_9$OCH$_2$F | Overall = | 0.6% |
| | | | 0.3% sec-C$_4$F$_9$OCH$_2$F | Iso = | 0% |
| | | | 0% i-C$_4$F$_9$OCH$_2$F | Normal = | 0.8% |
| | | | 38.4% n-C$_3$F$_7$CO$_2$CH$_2$CH$_3$ | | |
| | | | 60.9% i-C$_3$F$_7$CO$_2$CH$_2$CH$_3$ | | |
| 1522 | −75 | 6 | 3.2% n-C$_4$F$_9$OCH$_2$F | Overall = | 0.6% |
| | | | 0.5% sec-C$_4$F$_9$OCH$_2$F | Iso = | 0% |
| | | | 0% i-C$_4$F$_9$OCH$_2$F | Normal = | 7.8% |
| | | | 37.6% n-C$_3$F$_7$CO$_2$CH$_2$CH$_3$ | | |
| | | | 58.8% i-C$_3$F$_7$CO$_2$CH$_2$CH$_3$ | | |
| 1328 | −30 | 5 | 0.3% n-C$_4$F$_9$OCH$_2$F | Overall = | 0.6% |
| | | | 0.3% sec-C$_4$F$_9$OCH$_2$F | Iso = | 0% |
| | | | 0% i-C$_4$F$_9$OCH$_2$F | Normal = | 0.8% |
| | | | 38.4% n-C$_3$F$_7$CO$_2$CH$_2$CH$_3$ | | |
| | | | 60.9% i-C$_3$F$_7$CO$_2$CH$_2$CH$_3$ | | |
| 1701 | −74 | 7 | 4.0% n-C$_4$F$_9$OCH$_2$F | Overall = | 4.4% |
| | | | 0.4% sec-C$_4$F$_9$OCH$_2$F | Iso = | 0% |
| | | | 0% i-C$_4$F$_9$OCH$_2$F | Normal = | 11.0% |
| | | | 32.5% n-C$_3$F$_7$CO$_2$CH$_2$CH$_3$ | | |
| | | | 63.0% i-C$_3$F$_7$CO$_2$CH$_2$CH$_3$ | | |

The data for the normal isomer illustrates the reversibility of this catalytic alkylation reaction and the sensitivity of the equilibrium position to temperature, with the equilibrium shifting in favor of the ether product as the temperature is lowered. The lack of any measurable alkylation of the iso-C$_3$F$_7$COF isomer is further evidence of the detrimental impact of R$_f$ branching on alkylation yields. The measurable but relatively low alkylation yields obtained for the normal isomer compared to similar reactions with CH$_3$F reflect the relatively less favorable equilibrium constants for acid fluoride alkylations employing CH$_2$F$_2$ versus CH$_3$F as the alkylating agent. The source of the sec-C$_4$F$_9$OCH$_2$F product isomer is not certain, although this product could be derived from alkylation of perfluoro-2-butanone (CF$_3$CF$_2$COCF$_3$) formed by HSbF$_6$ catalyzed rearrangement of the 4-membered ring cyclic ether, cyclo-CF$_2$CF$_2$CF(CF$_3$)O. The latter cyclic ether has been detected as an impurity in ECF-derived perfluorobutyryl fluorides.

Example 4
Synthesis of perfluoroisopropyl methyl ether (i-C$_3$F$_7$OCH$_3$) from the HSbF$_6$ catalyzed reaction of hexafluoropropylene oxide (HFPO) with CH$_3$F by in situ formation of hexafluoroacetone as an intermediate.

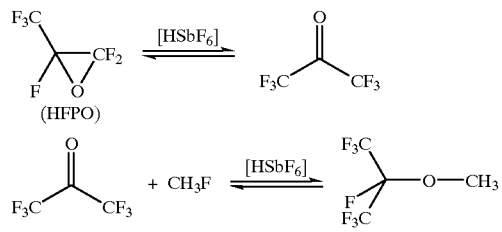

Using essentially the procedure of Example 1, the reactor was initially charged with 2.02 g of SbF$_5$ catalyst (Aldrich) then with 66.7 g hexafluoropropylene oxide (HFPO, Aldrich, 98%) while stirring and maintaining dry ice cooling. A temperature increase to −28° C. was observed upon completion of HFPO addition. After stirring the reaction mixture for 10 minutes in a dry ice bath to allow the reaction temperature to return to −60° C., the reactor was pressurized to 10 p.s.i. (775 torr) with nitrogen gas and a ~1 g sample of the cold reaction mixture was removed through the dip tube and immediately quenched in 30 mL methanol at approximately −70° C. (aliquot #1), as described in Example 1. The resulting methanol solution was stirred for at least 30 minutes at −70° C. before gradual warming to room temperature to ensure complete methanolysis of the reaction components. The methanol solution then was analyzed by GC, GC-MS and NMR in order to determine the distribution of quenching products.

It is known that HFPO reacts with methanol under these conditions to form CF$_3$CF(OCH$_3$)CO$_2$CH$_3$ whereas hexafluoroacetone gives primarily CF$_3$C(OH)(OCH$_3$)CF$_3$ along with small amounts of CF$_3$C(OH)$_2$CF$_3$ from hydrolysis. Therefore the relative amounts of these quenching products provides a measure of the percent HFPO and hexafluoroacetone present in the reactor just prior to quenching. As can be seen from the tabulated results for aliquot #1 in Table 4 below, the reaction mixture at this point was comprised of approximately 98% hexafluoroacetone, with only 2% HFPO remaining unreacted.

The Parr reactor, with its remaining contents held at approximately −60° C., was then charged with 30.0 g of gaseous CH$_3$F (Purity=98$^+$%, PCR) with stirring. Methyl fluoride addition caused the reaction temperature to rise to −42° C. The reaction temperature was quickly returned to −70° C. through dry ice cooling and this temperature was maintained for a period of hours during which additional reaction aliquots were removed, quenched and analyzed (as described above) to determine the reaction composition and percent conversion to the alkylation product, i-C$_3$F$_7$OCH$_3$, as a function of time. The quenched reaction aliquots were analyzed directly as the methanol solution. Additionally, in some cases, a portion of the methanol solution collected was treated with an equal volume of water to cause the liquid fluorochemical components to phase split as a separate lower phase which was then isolated and independently analyzed by GC, GC-MS and NMR. Alkylation was found to be essentially complete after 4.5 hours at −70° C. (following the addition of methyl fluoride), as shown by the tabulated analytical data for aliquot #3.

Using essentially the procedure of Example 1, the reactor was initially charged with 1.798 g of $HSbF_6$ catalyst (Aldrich) and then with 71.80 g of gaseous $C_2F_5COF$ (Purity=97%; Major impurities include 1.5% $CF_3CF_2OCF_3$ and 0.5% cyclo-$CF_2CF_2CF_2O$) while maintaining dry ice cooling. The reactor then was charged in similar fashion

TABLE 4

| Overall Reaction Time (min) | Reaction Temp. (° C.) | Aliquot # (or comment) | Product Distribution in Methanol Solution by GC Area % (and Wt % by NMR) | | Product Distribution in Fluorochemical Phase by GC Area % (and Wt % by NMR) |
|---|---|---|---|---|---|
| 13 | −60 | 1 | $CF_3C(OH)(OCH_3)CF_3$ | 97.2% (98.1%) | — |
|  |  |  | $CF_3C(OH)_2CF_3$ | 0.5% (0.7%) |  |
|  |  |  | $CF_3CF(OCH_3)CO_2CH_3$ | 2.3% (1.2%) |  |
| 17 | −64 | Begin charging $CH_3F$ | — |  |  |
| 285 | −69 | 3 | $CF_3CF(OCH_3)CF_3$ | 98.3% | $CF_3CF(OCH_3)CF_3$ |
|  |  |  | $CF_3CF(OCH_3)CF_2OC_3F_7$ | 1.6% | 92.4% (93.4%) |
|  |  |  | $CF_3C(OH)(OCH_3)CF_3$ | 0.02% | $CF_3CF(OCH_3)CF_2OC_3F_7$ |
|  |  |  | $CF_3C(OH)_2CF_3$ | 0% | 7.1% (6.2%) |
|  |  |  | $CF_3CF(OCH_3)CO_2CH_3$ | 0% | $CF_3C(OH)OCH_3)CF_3$ |
|  |  |  |  |  | 0.1% (0%) |
|  |  |  |  |  | $CF_3C(OH)_2CF_3$ |
|  |  |  |  |  | 0% (0%) |
|  |  |  |  |  | $CF_3CF(OCH_3)CO_2CH_3$ |
|  |  |  |  |  | 0.3% (0.3%) |

Thus, HFPO rapidly isomerizes almost completely to hexafluoroacetone in the presence of catalytic amounts of $HSbF_6$ at low temperatures The hexafluoroacetone which is generated in situ in turn undergoes $HSbF_6$ catalyzed alkylation by methyl fluoride at low temperatures and in nearly quantitative yield to give the highly fluorinated ether, i-$C_3F_7OCH_3$. The only significant byproduct detected is $CF_3CF(OCH_3)CF_2OC_3F_7$, which is believed to form by $HSbF_6$ catalyzed dimerization of HFPO to the intermediate ketone, $CF_3COCF_2OC_3F_7$, which also is then catalytically alkylated by methyl fluoride. Subsequent heating of the reaction mixture to 0° C. after collecting aliquot #3 resulted in essentially no change in the reactant/product distribution as determined by analysis of the methanol quenching products. This indicates that either the alkylation equilibrium for hexafluoroacetone is relatively insensitive to temperature, or that the $HSbF_6$ catalyst was somehow inadvertently deactivated (or poisoned) prior to warming the reaction mixture.

Example 5

$HSbF_6$ catalyzed reaction of perfluoropropionyl fluoride ($C_2F_5COF$) with ethylene and excess HF to produce n-$C_3F_7OCH_2CH_3$ by in situ generation of ethyl fluoride (or its equivalent):

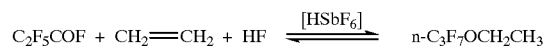

with 31.6 g anhydrous HF and 27.6 g ethylene (99.5+%, Aldrich), in that order. The ethylene was added slowly to minimize the reaction exotherm.

Once all the reagents were charged at −70° C., the progress of the reaction was monitored as a function of temperature by periodically removing reaction aliquots through the dip tube and quenching in methanol as previously described in Example 1 to destroy the catalyst and convert any unreacted $C_2F_5COF$ to the corresponding methyl ester. The resulting methanol solutions were analyzed by GC after warming to room temperature. A portion of each methanol solution was treated with an equal volume of chilled water to cause the fluorinated components to phase split as a separate lower liquid phase. The liquid fluorochemical phase was isolated and analyzed independently by GC. Selected samples also were subjected to GC-MS analysis to confirm GC peak assignments. Analytical results for each aliquot are summarized in Table 5 below. Since the methanol solution and the isolated fluorochemical phase for each aliquot gave virtually identical distributions of quenching products, only the results for the methanol solution are shown.

TABLE 5

| Reaction Time (min) | Pressure (torr) | Temp (° C.) | Aliquot # And Comments | Product Distribution in Methanol Solution by GC Area % |
|---|---|---|---|---|
| 74 | 2740 | −67 | Addition of all reactants complete. |  |
| 146 | 2070 | −70 | Aliquot #1 | $C_2F_5CO_2CH_3$ 69% |
|  |  |  |  | n-$C_3F_7OC_2H_5$ 31% |
|  |  |  |  | [Alkylation Yield = 31%] |

TABLE 5-continued

| Reaction Time (min) | Pressure (torr) | Temp (° C.) | Aliquot # And Comments | Product Distribution in Methanol Solution by GC Area % | |
|---|---|---|---|---|---|
| 300 | 1750 | −70 | Aliquot #2, Gradual pressure drop probably due to slow ethylene polymerization. | $C_2F_5CO_2CH_3$<br>n-$C_3F_7OC_2H_5$<br>[Alkylation Yield = 27%] | 73%<br>27% |
| 362 | 2380 | −16 | Aliquot #3, Insoluble polyethylene oil observed as separate phase in MeOH quench. | $C_2F_5CO_2CH_3$<br>n-$C_3F_7OC_2H_5$<br>[Alkylation Yield = 36%] | 64%<br>36% |
| 408 | 1030 | −71 | Aliquot #4, Insoluble polyethylene oil observed as separate phase in MeOH quench. | $C_2F_5CO_2CH_3$<br>n-$C_3F_7OC_2H_5$<br>[Alkylation Yield = 34%] | 66%<br>34% |

The maximum conversion to n-$C_3F_7OC_2H_5$ measured was 36%, similar to what was achieved in a separate experiment employing ethyl fluoride (instead of ethylene+ HF) as the alkylating agent (see Example 9). In addition to the quenching products listed in Table 5 above, later aliquots (#3 and 4) also contained significant quantities of a byproduct identified by GC-MS as a mixture of polyethylene oligomers, some of which contained a single fluorine atom. The polyethylene oligomers are presumably formed by acid initiated cationic polymerization of the ethylene reactant, which apparently competes with the catalytic alkylation reaction, especially at elevated temperatures, and eventually appears to lead to catalyst poisoning. Similar evidence of ethylene polymerization was observed using ethyl fluoride as the alkylating agent (Example 9).

Example 6

This example describes experiments designed to assess the relative activities of various acids as catalysts for the reversible alkylation reaction shown below

$$C_3F_7COF + CH_3F \xrightleftharpoons[]{[Catalyst]} C_4F_9OCH_3$$

Since it has been established that this reaction is a reversible equilibrium, and therefore governed by the principle of microscopic reversibility, any catalyst which catalyzes the forward reaction will also catalyze the reverse reaction and vice versa Thus, a simple and convenient method was developed for catalyst screening which involves the reaction of a pure sample of the hydrofluoroether, $C_4F_9OCH_3$ (65:35 iso:normal isomer mixture, available from 3M Company as HFE-7100™ fluorinated fluid) with a small amount of each potential catalyst under ambient conditions and qualitatively assessing catalyst activity by comparing the relative rates of dealkylation. Barring interference from catalyst poisons, those catalysts which provide the highest activity for dealkylation (reverse reaction) will be the most active for alkylation (forward reaction) as well.

In the experimental procedure, a small amount, typically 0.1 to 0.5 grams, of the potential catalyst was loaded into an oven-dried, 10 mL glass vial and approximately 3 to 4 grams of the test hydrofluoroether was added at room temperature with minimal exposure of the catalyst mixture to ambient air. The vials were loosely capped to allow any evolved gases to escape. Catalyst activity was judged qualitatively from the observed relative rates of gas ($CH_3F+C_3F_7COF$) evolution and the extent of evaporative cooling of the reaction mixtures for each catalyst. If no reaction was apparent at ambient temperatures, the contents of the vial were heated briefly to reflux temperature using a hand held heat gun and the vial monitored for apparent reaction. The formation of $C_3F_7COF$ was confirmed by its characteristic odor, and in some cases by quenching the partially converted reaction mixture with methanol and identification of the methyl ester by GC analysis. Since the screening reactions were conducted in ambient air and certain catalysts are sensitive to poisoning by moisture and other agents, lack of apparent activity in this screening test is not necessarily dispositive of catalytic activity. The following results were obtained.

a) $SbF_5$: The addition of the hydrofluoroether to antimony pentafluoride led to an instantaneous and rapid evolution of gas which was determined to be a mixture of $C_3F_7COF$ and $CH_3F$. The reaction proceeds until the ether has been completely consumed.

b) $HSbF_6$: In a similar manner, hexafluoroantimonic acid was found to be catalytically active at ambient temperature. As with $SbF_5$, the reaction occurs instantly and with rapid evolution of gas and continues until the hydrofluoroether has been completely consumed. The $HSbF_6$ appeared to be slightly more active than $SbF_5$ under similar conditions.

c) 4 $FSO_3H.SbF_5$: This catalyst, available as Magic Acid™ from Aldrich Chemical Company, displayed catalytic activity comparable to $HSbF_6$. Reaction was instantaneous and gave rise to rapid gas evolution until all hydrofluoroether was consumed.

d) $SbCl_5$: Antimony pentachloride is soluble in the hydrofluoroether to give a clear slightly yellow solution. Although no gas evolution was noted at first, the solution gradually became cloudy with a white, milky appearance. On slight warming (body heat from hand), the solution became transparent once again and began to evolve gas. The gas was determined to contain $C_3F_7COF$ by detection of its very characteristic odor. Though not as immediately active as the previous two catalysts, antimony pentachloride does exhibit latent catalytic activity for this reaction.

e) $AlCl_3$: No catalytic activity was observed at ambient temperature, but upon heating to brief reflux $C_3F_7COF$ was again detected by its odor. In this case, the reaction did not proceed to completion.

f) $AlCl_nF_{(3-n)}$ (ACF): This catalyst was prepared according to the method described in U.S. Pat. No. 5,157,171, Example 1. The catalyst was stored and loaded into the glass test vial in a nitrogen-filled drybox in order to minimize exposure to moisture, which can reportedly lead to catalyst poisoning. Reaction with the hydrofluoroether was conducted in ambient air as described above. Initial catalytic activity was moderate, but significantly less than $SbF_5$. Also, catalytic activity declined rapidly with time and was no longer detectable after 5 minutes, at which point most of the original hydrofluoroether charge still remained. The rapid loss in catalytic activity in this instance may have been due to poisoning by atmospheric moisture.

g) $SiO_2/AlCl_2$: This catalyst was prepared according to the method of R. Drago in Inorg. Chem. 29, 1186 (1990) and handled in a fashion similar to that described for ACF to minimize exposure to ambient moisture. Initial catalytic activity was very low and, as with ACF, declined to the point where it was undetectable in less than 5 minutes.

h) 1:1 $HC(SO_2CF_3)_3/SbF_5$ (by wt.): The tris-(trifluoromethanesulfonyl)methane acid was prepared according to the method described in U.S. Pat. No. 5,554,664, Example 1 and combined with an equal weight of $SbF_5$ in a nitrogen-filled drybox. The catalyst mixture was loaded into a glass test vial and removed from the drybox for subsequent reaction with the hydrofluoroether in ambient air. Initial catalytic activity was moderate, comparable to ACF and significantly less than pure $SbF_5$.

Example 7

In addition to determining the relative reactivities of various catalysts, one can use test methods identical to those described above for Example 6 to determine the relative reactivities of various hydrofluoroethers toward catalytic dealkylation by a given catalyst at ambient temperature. When combined with calculated thermodynamic parameters for a given equilibrium reaction, this information can be useful in predicting whether a particular ether structure can be more or less easily prepared by the catalyzed reaction of the appropriate carbonyl precursor with an appropriate alkylating agent. One also gains insight into the lifetime of the catalyst at room temperature in the presence of the various reaction components by this test. The following results were obtained for a series of different hydrofluoroethers using either $SbF_5$ or $HSbF_6$ as the catalyst where the indicated hydrofluoroether was reacted with the catalyst in the manner described in Example 6.

a) $C_4F_9OC_2H_5$ (60:40, n- to iso): Catalytic dealkylation with $HSbF_6$ to produce ethyl fluoride and $C_3F_7COF$ is rapid initially, but the rate of reaction quickly decreases and then stops, possibly due to deactivation of the catalyst by the ethyl fluoride by-product. Further experiments demonstrated that $C_4F_9OC_2H_5$ can be prepared from ethyl fluoride and $C_3F_7COF$ at lower temperatures where the antimony catalysts retain their activity for significantly longer periods of time.

b) n- and i-$C_4F_9OCH_3$: In a comparison of the rates of reaction of the normal and iso isomers, pure samples of each isomer were reacted with $SbF_5$ at room temperature. In these side by side experiments, the iso isomer was completely consumed in 5 minutes whereas the normal isomer required 14 minutes.

c) $C_2F_5CF(OCH_3)CF(CF_3)_2$: $HSbF_6$ catalyst caused vigorous gas evolution at room temperature. The starting material was consumed completely and the product which remained in the flask was determined to be $C_2F_5COCF(CF_3)_2$ by IR and GCMS analysis.

d) Methoxyperfluorocyclohexane: In this case, it was found that $HSbF_6$ did not rapidly catalyze the decomposition of the ether at room temperature. However $SbF_5$ did catalyze the rapid decomposition of the ether at room temperature to give significant amounts of perfluorocyclohexanone, as determined by GC e) $C_4F_9OCH_2F$: $HSbF_6$ catalyst caused vigorous gas evolution at room temperature. The starting ether was completely consumed in a short time. The gas evolved is presumably $CH_2F_2$, but this was not confirmed.

f) $C_4F_9OC_3H_7$: With $SbF_5$ there is initial reaction to give the corresponding acid fluoride but reaction rapidly ceases due to catalyst deactivation. As with the $C_4F_9OC_2H_5$ above, the fluoropropane formed in the dealkylation may react with the catalyst to deactivate it at room temperature, although the detailed mechanism of deactivation is not clear.

g) $C_6F_{13}OCF_2H$: With $SbF_5$ there is very rapid reaction to give $C_5F_{11}COF$ and $CF_3H$. The presence of the $CF_3H$ was confirmed by gas cell infrared spectroscopy of the effluent gases.

h) $C_4F_9O(C_2F_4O)_2CF_2H$: As in (g) above there is very rapid reaction with $SbF_5$ to give $C_4F_9OC_2F_4OCF_2COF$ and $CF_3H$ as the sole products.

i) $C_8F_{17}OCH_2CF_3$: With $SbF_5$ there is a very short initial reaction but the catalytic activity is quickly lost and the material is not visibly consumed. There is no $C_7F_{15}COF$ detected by GLC of the methanol washed product (to form the methanol ester). Again, a lower temperature alkylation may still be successful.

j) $C_4F_9OCH_2Cl$: With $SbF_5$ there was an initial rapid reaction to produce the $C_3F_7COF$ but again the catalytic activity was quickly lost. With $HSbF_6$ there was initial vigorous evolution of gas but the catalyst quickly was deactivated and formed a red-brown solid of unknown composition.

k) $C_4F_9OCHCl_2$: With $HSbF_6$ there was essentially an identical reaction to that observed in (j), rapid but short reaction with conversion of the catalyst to a red-brown solid.

Example 8

$HSbF_6$ acid catalyzed reaction of perfluoroethylisopropyl ketone with methyl fluoride to produce 3-methoxy-perfluoro-2-methylpentane

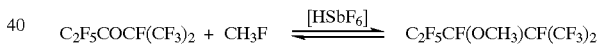

A 600 mL Parr Bench Top Mini Reactor equipped with a mechanical stirrer, thermocouple probe, dip tube, and pressure gauge was dried in an oven at 125° C. for two hours. The ambient temperature reactor was reassembled after the addition of 91 g of $C_2F_5COCF(CF_3)_2$ (Purity 99.6%) and evacuated to 2 Torr at −78° C. The reactor was charged with 10 grams of $HSbF_6$ from a 150 mL monel cylinder. While maintaining dry ice cooling on the reactor 48 g $CH_3F$ (purity=98+%, PCR) was charged to the reactor. Once all the reagents were charged, the reactor was cooled with a dry ice bath overnight. A leak in the Teflon head seal developed overnight, which was repaired and the reactor repressurized with helium. Gas chromatographic analysis of a reaction aliquot sampled at −55° C. and quenched in methanol as described in Example 1 indicated that 25% of the starting material was converted to product. The reaction was held over the weekend with a dry ice bath and was at −6° C. when sampled as Aliquot 2. The reaction was cooled to −50° C. and Aliquot 3 was taken. Another leak developed and the run was stopped. The procedure employed to collect, quench, work up and analyze each reaction aliquot was similar to that described in Example 1. The results of this study, including the composition of the isolated fluorochemical phase and the calculated percent conversion at each temperature are summarized in Table 6 below:

TABLE 6

| Overall Reaction Time (min) | Reaction Temp. (° C.) | Aliquot # | Fluorochemical Composition (by GC Area %) | Percent Conversion [ether]/([ether] + [ketone]) × 100 |
|---|---|---|---|---|
| 1020 | −55 | 1 | 74.6% $C_2F_5COCF(CF_3)_2$<br>25.0% $C_2F_5CF(OCH_3)CF(CF_3)_2$ | Overall = 25.1% |
| 2400 | −6 | 2 | 96.6% $C_2F_5COCF(CF_3)_2$<br>2.6% $C_2F_5CF(OCH_3)CF(CF_3)_2$ | Overall = 2.7% |
| 2505 | −50 | 3 | 58.4% $C_2F_5COCF(CF_3)_2$<br>41.5% $C_2F_5CF(OCH_3)CF(CF_3)_2$ | Overall = 41.5% |

This reaction shows that a substantial amount of perfluorinated ketone is converted to ether product even under non-ideal conditions, i.e. low levels of $CH_3F$ due to gas leak. Aliquot I was analyzed by GC-MS to confirm product identification.

Example 9

$HSbF_6$ catalyzed reaction of perfluoropropionyl fluoride with ethyl fluoride to produce 1-ethoxy-perfluoropropane

A 600 mL Parr Bench Top Mini Reactor equipped with a mechanical stirrer, thermocouple probe, dip tube, and pressure gauge was cleaned with acetone and evacuated to 1 Torr to remove residual acetone. The evacuated reactor was charged with 101.5 g of liquefied $C_2F_5COF$ (Purity 97%; Major impurities include 1.5% $CF_3CF_2OCF_3$ and 0.5% cyclo-$CF_2CF_2CF_2O$) while maintaining dry ice cooling. The reactor was then charged with 10 g $HSbF_6$ catalyst (Aldrich) per Example 8 and cooled to −50° C. While maintaining dry ice cooling, the reactor was charged with 48 g of gaseous $C_2H_5F$ (Purity=97% min, PCR) through the head space of the reactor. Samples were taken at various temperatures per the procedure outlined in Example 1, but using ethanol instead of methanol as the quenching agent. The product distribution and percent conversion determined by GC analysis of the fluorochemical phase isolated after water addition to the alcohol quench solution are summarized in Table 7.

TABLE 7

| Overall Reaction Time (min) | Reaction Temp. (° C.) | Aliquot # (or comment) | Fluorochemical Composition (by GC Area %) | Percent Conversion [ether]/([ether] + [ester]) × 100 |
|---|---|---|---|---|
| 15 | −50 | 1 | 70.8% $C_2F_5CO_2C_2H_5$<br>18.3% $C_3F_7OC_2H_5$<br>10.5% $C_2H_5F$<br>0.4% Polyethylene oligomers | Overall = 20.5% |
| 120 | −64 | 2 | 63.3% $C_2F_5CO_2C_2H_5$<br>21.2% $C_3F_7OC_2H_5$<br>9.7% $C_2H_5F$<br>0.4% Polyethylene oligomers | Overall = 25.1% |
| 1140 | −37 | 3 | 63.3% $C_2F_5CO_2C_2H_5$<br>32.5% $C_3F_7OC_2H_5$<br>6.7% $C_2H_5F$<br>6.8% Polyethylene oligomers | Overall = 37.6% |
| 1200 | −37 | 4 | 54.3% $C_2F_5CO_2C_2H_5$<br>31.6% $C_3F_7OC_2H_5$<br>7.0% $C_2H_5F$<br>7.1% Polyethylene oligomers | Overall = 36.7% |
| 1270 | −42 | 5 | 49.8% $C_2F_5CO_2C_2H_5$<br>27.7% $C_3F_7OC_2H_5$<br>3.4% $C_2H_5F$<br>7.2% Polyethylene oligomers | Overall = 31.0% |
| 1410 | −58 | 6 | 49.8% $C_2F_5CO_2C_2H_5$<br>32.9% $C_3F_7OC_2H_5$<br>8.5% $C_2H_5F$<br>8.8% Polyethylene oligomers | Overall = 39.8% |
| 1560 | −55 | 7 | 51.8% $C_2F_5CO_2C_2H_5$<br>33.2% $C_3F_7OC_2H_5$<br>6.7% $C_2H_5F$<br>8.3% Polyethylene oligomers | Overall = 39.0% |

This reaction shows that fluoroethane can be used as an effective alkylating agent in this reaction although competing formation of polyethylene oligomers is observed under the reaction conditions.

Example 10

$HSbF_6$ acid catalyzed reaction of perfluoropropionyl fluoride with methyl fluoride to produce 1-methoxy-perfluoropropane

A 600 mL Parr Bench Top Mini Reactor equipped with a mechanical stirrer, thermocouple probe, dip tube, and pressure gauge was cleaned with acetone and evacuated to 1 Torr to remove residual acetone. The reactor was charged with 11.3 g HSbF$_6$ catalyst (Aldrich) per Example 8 and cooled with dry ice. The evacuated reactor was charged with 105.5 g of liquefied, sulfuric acid treated, C$_2$F$_5$COF (Purity 97%; Major impurities include 1.5% CF$_3$CF$_2$OCF$_3$ and 0.5% cyclo-CF$_2$CF$_2$CF$_2$O) while maintaining dry ice cooling. [The sulfuric acid treatment of C$_2$F$_5$COF consists of washing it with a 10% weight charge of concentrated sulfuric acid in a clean dry Parr reactor at ambient conditions for one hour. The C$_2$F$_5$COF is then transferred to a clean dry stainless steel cylinder by one plate distillation from the reactor into the dry ice cooled cylinder. The Parr reactor is heated to 30° C. to complete the one plate distillation of the C$_2$F$_5$COF to the cylinder.] Following the addition of sulfuric acid purified C$_2$F$_5$COF to the Parr reactor the reactor is charged with 43.5 g of gaseous CH$_3$F (Purity=98$^+$% PCR) through the head space of the reactor while maintaining dry ice cooling. Samples were taken at various temperatures per Example 9. The overall GC results from this study are summarized in Table 8.

TABLE 8

| Overall Reaction Time (min) | Reaction Temp. (° C.) | Aliquot # | Fluorochemical Composition (by GC Area %) | Percent Conversion [ether]/([ether] + [ester]) × 100 |
| --- | --- | --- | --- | --- |
| 15 | −50 | 1 | 48.2% C$_2$F$_5$CO$_2$C$_2$H$_5$ 51.2% C$_3$F$_7$OCH$_3$ | Overall − 51.5% |
| 1125 | −47 | 2 | 20.8% C$_2$F$_5$CO$_2$C$_2$H$_5$ 79.0% C$_3$F$_7$OCH$_3$ | Overall = 79.1% |
| 1245 | −64 | 3 | 38.1% C$_2$F$_5$CO$_2$C$_2$H$_5$ 61.7% C$_3$F$_7$OCH$_3$ | Overall = 61.8% |
| 1350 | −46 | 4 | 13.7% C$_2$F$_5$CO$_2$C$_2$H$_5$ 86.3% C$_3$F$_7$OCH$_3$ | Overall = 86.3% |
| 1385 | −30 | 5 | 11.5% C$_2$F$_5$CO$_2$C$_2$H$_5$ 88.3% C$_3$F$_7$OCH$_3$ | Overall = 88.5% |
| 1465 | −37 | 6 | 6.4% C$_2$F$_5$CO$_2$C$_2$H$_5$ 93.6% C$_3$F$_7$OCH$_3$ | Overall = 93.6% |
| 2445 | −19 | 7 | 40.0% C$_2$F$_5$CO$_2$C$_2$H$_5$ 59.9% C$_3$F$_7$OCH$_3$ | Overall = 60.0% |
| 2555 | −41 | 8 | 6.1% C$_2$F$_5$CO$_2$C$_2$H$_5$ 92.4% C$_3$F$_7$OCH$_3$ | Overall = 93.8% |

This reaction provides high conversions to the desired ether products, and the catalyst lifetime is extremely long.

Example 11

SbF$_5$ catalyzed transalkylation reaction of pentafluoropropionyl fluoride with 2-H-octafluoroisobutylmethyl ether to produce heptafluoropropylmethyl ether.

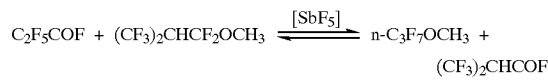
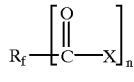

In a tubular, stainless steel pressure reactor pentafluoropropionyl fluoride (3.39 g, purity 97% 23 mmol), 2-H octafluoroisobutylmethyl ether (6.17 g, purity 98%, 26 mmol) and antimony pentafluoride (Aldrich, 0.62 g, 3 mmol) were heated at 50–52° C. for 24 hours. A pressure of 9300 torr at 50° C. was achieved in 10 min after the reaction was begun and did not change upon further heating. The mixture was held overnight at −78° C. and then warmed to −10 to −15° C. for 5 hours. Methanol (3.1 g) was added at −78° C., the reactor was closed again, shaken and allowed to warm to room temperature for 30 min. After dismantling the reactor, 13.0 g of slightly colored liquid was recovered. The crude product was washed twice with water and dried over MgSO$_4$ to obtain 9.92 g of a mixture comprising 27% heptafluoro-n-propylmethyl ether (n-C$_3$F$_7$OCH$_3$); 1.3% 2-H-octafluoroisobutylmethyl ether; 4.1% methylpentafluoropropionate (C$_2$F$_5$COOCH$_3$) and 65% methyl-2H-hexafluoroisobutyrate (CF$_3$)$_2$CHCOOCH$_3$, by GC. The mixture was distilled to give 4.1 g n-C$_3$F$_7$OCH$_3$ (b.p. 34–52° C.; purity (GC)=75%) and 5.0 g (CF$_3$)$_2$CHCOOCH$_3$ (b.p. 76–90° C.; purity (GC)=93.5%; Product yields were calculated based upon the weight of starting materials charged and the weight of respective liquid product fractions isolated after correcting for purity as determined by GC. The yield of C$_3$F$_7$OCH$_3$ was 68% based upon pentafluoropropionyl fluoride and the yield of (CF$_3$)$_2$CHCOOCH$_3$ was 96% based on 2-H-octafluoroisobutylmethyl ether. The structure of all compounds was confirmed by $^{19}$F and $^1$H NMR.

We claim:

1. A process for the preparation of hydrofluoroether compounds, said process comprising:

(1) reacting in the presence of at least one Lewis acid catalyst or a mixture comprising Lewis acid and Bronsted acid catalysts:

a) a fluorinated ketene or a fluorinated carbonyl-containing compound of the formula:

$$R_f \!-\!\!\left[\!\!\begin{array}{c} O \\ \| \\ C\!-\!X \end{array}\!\!\right]_n$$

wherein n is an integer equal to 1, 2 or 3; and when n is 1, R$_f$ is a fluorine atom or is a fluorinated alkyl group having from 1 to about 15 carbon atoms that may be substituted or unsubstituted, saturated or unsaturated, cyclic or acyclic, linear or branched and may optionally contain one or more catenary heteroatoms;

when n is 2, R$_f$ is a fluorinated alkylene group having from 1 to about 15 carbon atoms that may be substituted or unsubstituted, saturated or unsaturated, cyclic or acyclic, linear or branched and may optionally contain one or more catenary heteroatoms;

when n is 3, $R_f$ is a fluorinated alkylidene group having from 1 to about 15 carbon atoms that may be substituted or unsubstituted, saturated or unsaturated, cyclic or acyclic, linear or branched and may optionally contain one or more catenary heteroatoms; and wherein each non-fluorine substituent on the above $R_f$ group may optionally include —Cl, —H, —Br, —SO$_2$X, —SO$_2$R', —COX —CO$_2$R', or —OR' where R' is a fluorinated or non-fluorinated alkyl group; and each X is independently a hydrogen or a halogen atom or is of the formula R'$_f$ or OR'$_f$ where R'$_f$ is a partially or fully fluorinated or non-fluorinated alkyl group having from 1 to about 10 carbon atoms that may be substituted or unsubstituted, saturated or unsaturated, cyclic or acyclic, linear or branched and may optionally contain one or more catenary heteroatoms; where X is an R'$_f$ group, that R'$_f$ group may form a ring with the $R_f$ group previously defined; and b) an alkylating agent of the formula:

R—F wherein:
R is a substituted or unsubstituted, saturated or unsaturated, cyclic or acyclic, linear or branched, non-halogenated or partially halogenated alkyl group having from 1 to about 10 carbon atoms that can optionally include one or more catenary heteroatoms, where if said R group is substituted, the non-hydrogen substituents may optionally include —Cl, —Br, —F, —SO$_2$X, —SO$_2$R', —COX', —COR', —CO$_2$R', or —OR' where R' is a fluorinated or non-fluorinated alkyl group and where X' is a halogen atom, and with the proviso that when R is perfluorinated, the R—F compound has an activated C—F bond; and (2) recovering hydrofluoroether from the resulting reaction mixture.

2. The process of claim 1 wherein said fluorinated carbonyl-containing compound is generated in situ from a fluorinated precursor compound during said reaction.

3. The process of claim 1 wherein said fluorinated carbonyl-containing compound is generated in situ from a fluorinated oxacycloalkane, ester, monoether or polyether.

4. The process of claim 1 wherein said fluorinated carbonyl-containing compound is a fluorinated acyl fluoride.

5. The process of claim 1 wherein fluorinated carbonyl-containing compound is a fluorinated ketone.

6. The process of claim 1 wherein said alkylating agent is CH$_3$F, C$_2$H$_5$F or CH$_2$F$_2$.

7. The process of claim 1 wherein said alkylating agent is generated in situ.

8. The process of claim 1 wherein said Lewis acid catalyst is SbF$_5$.

9. The process of claim 1 wherein said Lewis acid catalyst is HSbF$_6$.

10. The process of claim 1 wherein said fluorinated ketene is selected according to the formula:

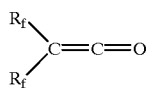

where each $R_f$ is selected, independently from one another, as a fluorine atom or as a fluorinated alkyl group having from 1 to about 15 carbon atoms that may be substituted or unsubstituted, saturated or unsaturated, cyclic or acyclic, linear or branched and may optionally contain one or more catenary heteroatoms such as nitrogen, sulfur, or oxygen.

11. The process of claim 1 wherein said fluorinated carbonyl-containing compound is perfluorinated.

12. The process of claim 11 wherein said fluorinated carbonyl-containing compound is selected from the group consisting of perfluorinated acyl fluorides, perfluorinated ketenes, and perfluorinated ketones.

13. The process of claim 1 wherein said alkylating agent and said fluorinated carbonyl-containing compound are covalently linked.

14. The process of claim 1 wherein said catalyst is selected from the group of compounds consisting of: SbF$_5$, HSbF$_6$, TiF$_4$, AlCl$_x$F$_{(3-x)}$(x=0–3) SbCl$_x$F$_{(5-x)}$(x=0–5), HF—BF$_3$, TaF$_5$, NbF$_5$, AsF$_5$, BiF$_5$, ZrF$_4$, FeF$_3$, SbCl$_5$, SbCl$_2$F$_3$, HOSO$_2$F/SbF$_5$, and mixtures and combinations thereof with each other or with HF or FSO$_3$H.

15. The process of claim 1 wherein said catalyst is supported on an inert substrate.

16. The process of claim 15 wherein said process is carried out continuously.

17. The process of claim 1 wherein said process is carried out in the absence of solvent.

18. A process for the preparation of hydrofluoroether compounds, said process comprising:

(1) reacting in the presence of at least one Lewis acid catalyst or a mixture comprising Lewis acid and Bronsted acid catalysts:
a) a fluorinated mono- or polyether compound or a fluorinated oxacycloalkane with
b) an alkylating agent of the general formula:

R—F wherein:
R is a substituted or unsubstituted, saturated or unsaturated, cyclic or acyclic, linear or branched, non-halogenated or partially halogenated alkyl group having from 1 to about 10 carbon atoms that can optionally include one or more catenary heteroatoms such as oxygen, nitrogen or sulfur, where if said R group is substituted, the non-hydrogen substituents may optionally include —Cl, —Br, —F, —SO$_2$X', —SO$_2$R', —COX', —COR', —CO$_2$R', or —OR' (where R' is as defined above and where X' is a halogen atom) and with the proviso that when R is perfluorinated, the R—F compound has an activated C—F bond; and (2) recovering hydrofluoroether from the resulting mixture.

19. The process of claim 18 wherein said mono- or polyether compound, or said fluorinated oxacycloalkane is perfluorinated.

20. The process of claim 18 wherein said fluorinated mono- or polyether compound is of the formula:

R$^1$O(R$^2$O)$_y$R$^3$ wherein y is 0 or is an integer greater than or equal to 1 and $R^1$, $R^2$, and $R^3$ each is independently selected as a non-fluorinated or a partially or fully fluorinated, substituted or unsubstituted, linear or branched, cyclic or acyclic, saturated or unsaturated alkyl group having from 1 to about 10 carbon atoms with the proviso that at least one of said $R^1$, $R^2$, or $R^3$ groups is fluorinated.

21. The process of claim 18 wherein said fluorinated oxacycloalkane is an oxacyclopropane.

22. The process of claim 18 wherein said catalyst is selected from the group of compounds consisting of: $SbF_5$, $HSbF_6$, $TiF_4$, $AlCl_xF_{(3-x)}$(x=0–3), $SbCl_xF_{(5-x)}$(x=0–5), $HF$—$BF_3$, $TaF_5$, $NbF_5$, $AsF_5$, $BiF_5$, $ZrF_4$, $FeF_3$, $SbCl_5$, $SbCl_2F_3$, $HOSO_2F/SbF_5$, and mixtures and combinations thereof with each other or with HF or $FSO_3H$.

23. The process of claim 18 wherein said catalyst is supported on an inert substrate.

24. The process of claim 23 wherein said process is carried out continuously.

25. The process of claim 18 wherein said process is carried out in the absence of solvent.

26. A process for the preparation of hydrofluoroether compounds, said process comprising:
(1) reacting in the presence of at least one Lewis acid catalyst or a mixture comprising Lewis acid and Bronsted acid catalysts:
a) a fluorinated mono- or polyether compound with
b) a fluorinated ketene or a fluorinated carbonyl-containing compound of the formula:

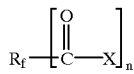

wherein n is an integer equal to 1, 2 or 3; and
when n is 1, $R_f$ is a fluorine atom or is a fluorinated alkyl group having from 1 to about 15 carbon atoms that may be substituted or unsubstituted, saturated or unsaturated, cyclic or acyclic, linear or branched and may optionally contain one or more catenary heteroatoms;

when n is 2, $R_f$ is a fluorinated alkylene group having from 1 to about 15 carbon atoms that may be substituted or unsubstituted, saturated or unsaturated, cyclic or acyclic, linear or branched and may optionally contain one or more catenary heteroatoms;

when n is 3, $R_f$ is a fluorinated alkylidene group having from 1 to about 15 carbon atoms that may be substituted or unsubstituted, saturated or unsaturated, cyclic or acyclic, linear or branched and may optionally contain one or more catenary heteroatoms; and wherein each non-fluorine substituent on the above $R_f$ group may optionally include —Cl, —H, —Br, —$SO_2X$, —$SO_2R'$, —COX, —$CO_2R'$, or —OR' where R' is a fluorinated or non-fluorinated alkyl group; and each X is independently a hydrogen or a halogen atom or is of the formula $R'_f$ or $OR'_f$ where $R'_f$ is a partially or fully fluorinated or non-fluorinated alkyl group having from 1 to about 10 carbon atoms that may be substituted or unsubstituted, saturated or unsaturated, cyclic or acyclic, linear or branched and may optionally contain one or more catenary heteroatoms; where X is an $R'_f$ group, that $R'_f$ group may form a ring with the $R_f$ group previously defined; and (2) recovering hydrofluoroether from the resulting mixture.

* * * * *

UNITED STATES PATENT AND TRADEMARK OFFICE
CERTIFICATE OF CORRECTION

PATENT NO. : 6,046,368
DATED : April 4, 2000
INVENTOR(S) : William M. Lamanna et al.

It is certified that error appears in the above-identified patent and that said Letters Patent is hereby corrected as shown below:

Column 7,
Line 3, please delete the word "Bronsted" and insert in place thereof -- Brønsted --.

Column 8,
Line 6, please delete "F5" and insert in place thereof -- $F_5$ --.

Column 9,
Line 43, please delete the word "Bronsted" and insert in place thereof -- Brønsted --.

Column 10,
Line 4, please delete the word "Bronsted" and insert in place thereof -- Brønsted --.

Column 12,
Line 23, please delete the word "extacting" and insert in place thereof -- extracting --.

Column 15,
Table 2, please delete "=71.6%" and insert in place thereof -- =59.2% --.
Table 2, please delete "5961" and insert in place thereof -- 5861 --.
Line 62, please delete "$C_4F_7COF$" and insert in place thereof -- $C_3F_7COF$ --.

Column 17,
Table 3, please delete "0.6%" and insert in place thereof -- 3.7% --.
Table 3, in the column heading entitled Overall Reaction Time (min), delete repeated table number 1328.

Column 25,
Line 17, please delete "I" and insert in place there -- 1 --.

UNITED STATES PATENT AND TRADEMARK OFFICE
CERTIFICATE OF CORRECTION

PATENT NO.   : 6,046,368
DATED        : April 4, 2000
INVENTOR(S)  : William M. Lamanna et al.

It is certified that error appears in the above-identified patent and that said Letters Patent is hereby corrected as shown below:

Column 26,
Table 7, in the third column under the heading "Aliquot #" please delete "(or comment)".
Table 7, please delete "63.3%" and insert in place thereof -- 54.0% --.
Table 7, please delete "49.8%" and insert in place thereof -- 61.7% --.

Column 31,
Line 25, please delete the word "Bronsted" and insert in place thereof -- Brønsted --.

Signed and Sealed this

Ninth Day of July, 2002

*Attest:*

*Attesting Officer*

JAMES E. ROGAN
*Director of the United States Patent and Trademark Office*